(12) United States Patent
Katzman

(10) Patent No.: US 11,832,885 B2
(45) Date of Patent: Dec. 5, 2023

(54) PATIENT HOME MONITORING AND PHYSICIAN ALERT FOR OCULAR ANATOMY

(71) Applicant: Sanovas Intellectual Property, LLC, Reno, NV (US)

(72) Inventor: Jerry Katzman, Tampa, FL (US)

(73) Assignee: Sanovas Intellectual Property, LLC, Reno, NV (US)

( * ) Notice: Subject to any disclaimer, the term of this patent is extended or adjusted under 35 U.S.C. 154(b) by 203 days.

(21) Appl. No.: 17/079,926

(22) Filed: Oct. 26, 2020

(65) Prior Publication Data

US 2021/0121062 A1 Apr. 29, 2021

Related U.S. Application Data

(60) Provisional application No. 62/925,301, filed on Oct. 24, 2019.

(51) Int. Cl.
*A61B 3/14* (2006.01)
*A61B 5/00* (2006.01)
*A61B 3/00* (2006.01)

(52) U.S. Cl.
CPC .............. *A61B 3/14* (2013.01); *A61B 3/0008* (2013.01); *A61B 5/0013* (2013.01); *A61B 5/0022* (2013.01); *A61B 5/0059* (2013.01); *A61B 5/742* (2013.01); *A61B 5/7405* (2013.01); *A61B 5/746* (2013.01); *A61B 5/7475* (2013.01)

(58) Field of Classification Search
CPC ............................ A61B 3/0008; A61B 5/7475

USPC ........................................................ 351/206
See application file for complete search history.

(56) References Cited

U.S. PATENT DOCUMENTS

| | | | |
|---|---|---|---|
| 7,465,049 B2 | 12/2008 | Maeda et al. |
| 7,802,884 B2 | 9/2010 | Feldon et al. |
| 8,262,221 B2 | 9/2012 | Filar |
| 8,836,778 B2 | 9/2014 | Ignatovich et al. |
| 9,504,380 B1 | 11/2016 | Quaid |
| 10,136,810 B2 | 11/2018 | Migliaccio et al. |
| 10,149,615 B2 | 12/2018 | Sakai et al. |
| 10,178,948 B2 | 1/2019 | Liu et al. |

(Continued)

FOREIGN PATENT DOCUMENTS

WO WO2019175679 9/2019

*Primary Examiner* — Fabricio R Murillo Garcia
(74) *Attorney, Agent, or Firm* — Blank Rome LLP

(57) ABSTRACT

A physician prescribes an ocular imaging unit to a patient, which the patient sets up in the home to self-monitor his/her ocular anatomy. Typically, the unit connects to a smartphone, and the patient can use an app to operate the system. When the patient experiences a problem with his/her eyes, the patient initiates a remote evaluation, and the system transmits an alert to a remotely located physician, signifying the need for a pre-diagnostic evaluation. The physician then performs an initial evaluation remotely over the Internet using the home ocular imaging unit to obtain images or live video of the patient's ocular anatomy. The physician remotely makes a pre-diagnostic assessment regarding whether an in-person diagnostic examination of the ocular anatomy is warranted, and then communicates this to the patient. In some cases, the imaging unit captures images, both of the retinas and exteriors of the eyes, and also performs vision tests.

22 Claims, 14 Drawing Sheets

(56) References Cited

U.S. PATENT DOCUMENTS

| | | |
|---|---|---|
| 2007/0118428 A1* | 5/2007 | Akiyama ................ A61B 3/112 |
| | | 351/206 |
| 2008/0259274 A1* | 10/2008 | Chinnock ................. A61B 3/14 |
| | | 351/206 |
| 2015/0150446 A1* | 6/2015 | Park ..................... A61B 3/0285 |
| | | 351/246 |
| 2018/0153399 A1 | 6/2018 | Fink et al. |
| 2019/0029516 A1* | 1/2019 | Fried ................... A61B 3/0285 |
| 2019/0082951 A1 | 3/2019 | Merriam et al. |
| 2019/0090733 A1 | 3/2019 | Walsh et al. |
| 2019/0148017 A1* | 5/2019 | Seriani ................... G16H 15/00 |
| | | 705/2 |
| 2019/0307324 A1 | 10/2019 | Limon |
| 2020/0093362 A1 | 3/2020 | Jackson et al. |
| 2020/0179168 A1 | 6/2020 | Kelleher et al. |

\* cited by examiner

PATIENT HOME MONITORING AND PHYSICIAN ALERT FOR OCULAR ANATOMY

FIELD OF THE INVENTION

The present invention relates to the home monitoring of a patient's ocular anatomy. More specifically, the invention relates to a home monitoring device deployed in the patient's home, from which an alert can be sent to a remotely located physician, who can then perform a pre-diagnostic evaluation remotely to assess whether an in-person medical diagnosis is warranted.

BACKGROUND OF THE INVENTION

Many patients require evaluation by physicians specializing in ocular anatomy, such as ophthalmologists and optometrists, due to the fact that there are a number of different eye conditions attributable to diseases and other pathologies arising in the eyes themselves, such as glaucoma, iritis, and cataracts, as well as those that are the result of other medical conditions, such as diabetes, arteritis, and neurological issues. The current model of eye care, in which patients schedule in-person visits with these eye specialists every time the patients are experiencing potential problems with their eyes, suffers from a number of drawbacks.

For example, a common condition for which screening is often necessary is diabetic retinopathy and maculopathy. Ocular screening is important because, when a patient has diabetes, the earliest observable change to the body is in the eyes. The eyes have the smallest blood vessels in the body, and therefore, any change affecting them is most easily detected in the eyes.

The retina is a nerve layer that lines the back of the human eye and that captures visual images and sends those images to the brain. Diabetic retinopathy is typically caused by changes in the retinal blood vessels, which are induced by high blood sugar levels in a diabetic patient. These changes lead to improper formation of the blood-retinal barrier and cause the retinal blood vessels to become weak and more permeable, and may result in bulges (microaneurysms) that can leak small amounts of blood. In some cases, the blood vessels in the macula (the central area of the retina) can also become blocked or leaky, resulting in diabetic maculopathy.

Not only is screening important for the purpose of diagnosing the diabetes itself, but diabetic retinopathy/maculopathy can be a serious condition and can often lead to poor vision or even blindness if it is not treated timely. Despite the importance of addressing the first signs of these conditions urgently, it is often difficult to schedule appointments with qualified eye care professional in a timely manner. Worldwide, there are over 500 million patients afflicted with this condition. Due their specialization, there are insufficient numbers of ophthalmologists and optometrists, both in the United States and globally, to screen, examine, diagnose and treat this volume of diabetic patients. There are simply not enough qualified specialists to handle the number of patients that actually have been diagnosed with diabetic retinopathy/maculopathy who require treatment, much less attend to the many patients that should have preventative screening and diagnoses, with the urgency that is often required.

This is only one example. There are, of course, many patients considered to be high-risk for loss of sight and blindness. Immediate intervention is needed for many types of disorders, not only for diabetic retinopathy/maculopathy as discussed above, but also for diabetic macula edema, macular degeneration (wet and dry), neurologic disorders, optic neuritis, hemorrhage, stroke, vascular disorders, cancer, and various other pathologies.

The existence of such existing problems has recently been further exacerbated by the current state of medical affairs. Specifically, the recent Coronavirus disease 2019 (COVID-19) caused by the severe acute respiratory syndrome coronavirus (SARS-CoV-2), which has resulted in a worldwide pandemic, appears to have both increased the demand for ocular evaluations, as well as the need to find an alternative to in-person diagnostic examinations.

In a large ophthalmologic study of patients with COVID-19 and diabetic maculopathy who were admitted to the hospital (N=1317), 260 patients were placed on respirators. Significantly, 10% died in the first week, and 46% had vascular changes in their peripheral retinas. This high percentage of microvascular changes may indicate a potential risk factor, and may be a critical, unrecognized sign of a higher risk in COVID-19 patients having diabetic maculopathy.

Compounding this problem is the simultaneous need to perform social distancing during the pandemic, which has greatly reduced the number of in-person office visits in which examinations can take place. In order to minimize the risk of exposure during these, it is important to be able to monitor at-risk patients without requiring an in-person office visit. This is especially important in view of the fact that more of the at-risk patients will be older, and these individuals are at much greater risk if exposed to COVID-19.

Accordingly, there is a need for a system enabling patients to self-monitor within their own home without having to wait for, and attend, in-person office visits every time a screening or non-diagnostic evaluation is warranted.

What is desired, therefor, is a patient monitoring system for ocular anatomy that enables a physician to be alerted when a potential problem exists. What is further desired is such a system that enables the physician to perform a quick, pre-diagnostic evaluation to make an initial assessment about the severity/urgency of the condition. What is also desired is such a system that does not require the patient to schedule and attend an in-person office visit.

SUMMARY OF THE INVENTION

Accordingly, it is an object of the present invention to provide a monitoring system for ocular anatomy that is compact and simple for a patient to set up and operate in their home.

It is also an object of the present invention to provide such a monitoring system that enables a remotely-located physician to be notified of the need to make an immediate pre-diagnostic assessment of the patient's ocular anatomy.

It is a further object of the present invention to provide such a monitoring system that enables a physician to perform a pre-diagnostic evaluation of the patient's ocular anatomy remotely.

In order to overcome the deficiencies of the prior art and to achieve at least some of the objects and advantages listed, the invention comprises a method of monitoring a patient's ocular anatomy, including receiving an evaluation initiation command from a patient's location where a patient is located, and upon receiving the evaluation initiation command, transmitting a physician alert from the patient's location over a network to a physician at a physician's location remote from the patient's location, the alert signifying a need for the physician to remotely evaluate the patient's ocular anatomy. The method further includes obtaining one or more images of the patient's ocular anatomy with an ocular imaging unit located at the patient's location, transmitting imaging data corresponding to the one or more images from the patient's location over the network to the physician's location remote from the patient's location, displaying one or more images from the imaging data at the physician's location for evaluation by the physician to make a pre-diagnostic assessment at the physician's location regarding whether an in-person diagnostic examination of the ocular anatomy is warranted, and communicating an instruction from the physician's location to the patient's location regarding whether an in-person diagnostic examination is warranted based on the pre-diagnostic assessment of the ocular anatomy.

In certain advantageous embodiments, the evaluation initiation command is generated by a personal computing device at the patient's location, the image of the patient's ocular anatomy is obtained with a separately housed ocular imaging unit that connects to the personal computing device, and the personal computing device transmits the physician alert to the physician's location via the Internet.

In some cases, the evaluation initiation command is generated by an audio command from the patient, an in other cases, the evaluation initiation command is input by the patient on a screen of the personal computing device.

In certain advantageous embodiments, the method further includes, prior to receiving an evaluation initiation command, prescribing to the patient the ocular imaging device, and storing patient-specific data associated with the patient, where transmitting the physician alert to the physician further includes transmitting the patient-specific data to the physician with the alert.

In some of these embodiments, the patient-specific data comprises physical characteristics of the patient's ocular anatomy and/or existing medical conditions of the patient.

In some cases, the instruction communicated from the physician's location to the patient's location indicates an in-person diagnostic examination is not warranted, and the method further includes receiving a second evaluation initiation command from the patient's location when the patient experiences an adverse event subsequent to the pre-diagnostic evaluation, and transmitting a second physician alert from the patient's location over the network to the physician at the physician's location remote from the patient's location.

In certain advantageous embodiments, the step of obtaining one or more images of the patient's ocular anatomy is performed in response to an image capture command from the remotely located physician after the physician alert is transmitted over the network to the physician at the physician's location. In other embodiments, the step of obtaining one or more images of the patient's ocular anatomy includes transmitting an instruction from the physician's location to the patient's location over the network after the physician alert is transmitted over the network to the physician's location, and, after receiving the instruction transmitted from the physician's location, receiving an image capture command from the patient at the patient's location.

In some cases, the one or more images comprise live video of the patient's ocular anatomy transmitted from the ocular imaging unit to the remotely located physician for viewing in real time.

In some embodiments, the one or more images of the patient's ocular anatomy is obtained with an ocular imaging unit including a first imaging section with a first objective lens, and a second imaging section with a second objective lens.

In some of these embodiments, the ocular imaging device includes a rotating portion including the first and second imaging sections, wherein the rotating portion rotates approximately 180 degrees such that each of the first and second imaging sections can be moved from a position adjacent a first eye of the patient to a position adjacent a second eye of the patient.

In certain embodiments, the first and second imaging sections are slidable relative to each other.

In certain advantageous embodiments, the first imaging section includes an illumination source that illuminates a retina of the patient when the patient looks through the first objective lens, and an image sensor that captures an image of the retina when the patient looks through the first objective lens and the retina is illuminated.

In some of these embodiments, the illumination source is a pulse of white light, and in some, the illumination source is near infrared light. In some cases, the second imaging section further comprises a light source that directs a fixation light into the optical path of the patient's eye for aligning the eye with the optical axis.

In some embodiments, the image sensor comprises a plurality of pixels, and the ocular imaging unit adjusts the intensity of the light received at each of the pixels to correct for uneven illumination.

In some embodiments, the image sensor is rotatable to capture an increased visible field of view.

In certain advantageous embodiments, the first imaging section includes an illumination source that illuminates the exterior of the eye, and an image sensor that captures an image of the exterior of the eye when the eye is illuminated.

In certain advantageous embodiments, the second imaging section includes a display that a patient views through the second objective lens, and a display illumination source that directs illumination onto the display to produce a virtual pattern for the patient to view through the second objective lens. After the physician makes the pre-diagnostic assessment at the physician's location and communicates an instruction from the physician's location to the patient's location regarding whether an in-person diagnostic evaluation is warranted, the ocular imaging unit enables the physician to remotely perform an initial diagnostic evaluation by receiving an audible statement from the patient corresponding to the patient's view of the virtual pattern on the display and transmitting the statement to the remotely located physician.

In some embodiments, the method further includes transmitting ocular measurement data derived at least in part from the obtained images.

DETAILED DESCRIPTION OF THE INVENTION

The following detailed description illustrates the technology by way of example, not by way of limitation, of the principles of the invention. This description will enable one skilled in the art to make and use the technology, and describes several embodiments, adaptations, variations, alternatives and uses of the invention, including what is presently believed to be the best mode of carrying out the invention. One skilled in the art will recognize alternative variations and arrangements, and the present technology is not limited to those embodiments described hereafter.

Figure 1:
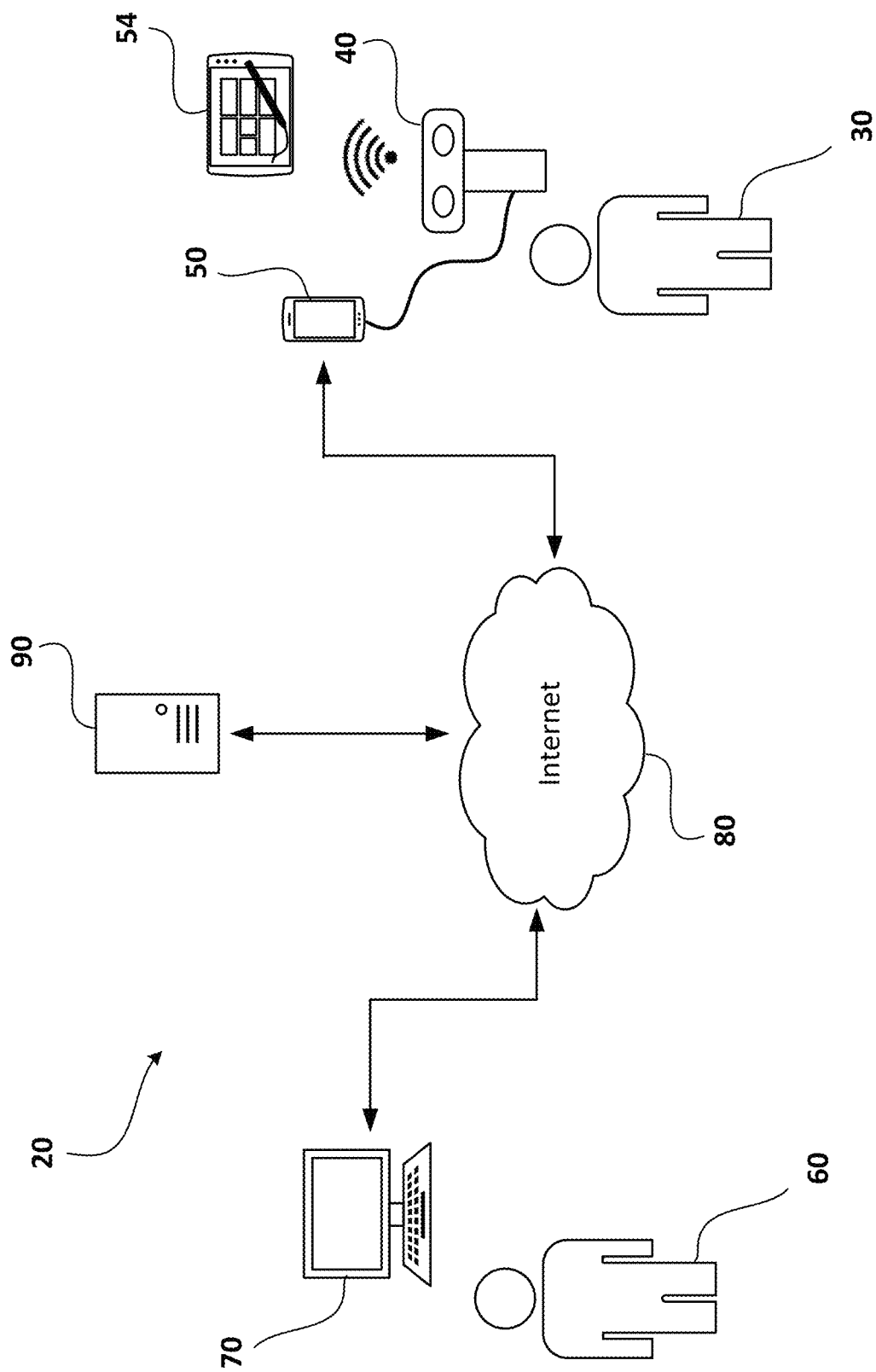
FIG. 1 is a schematic representation of a system according to exemplary embodiments of the present technology.

FIG. 1 illustrates one exemplary embodiment of a system (20) in accordance with the invention. In order to facilitate remote monitoring of the ocular anatomy of a patient (30), a home ocular imaging unit (40) is prescribed by the patient's physician (60). The imaging unit (40) may be provided to the patient (30) directly by the physician (60), or may be obtained by the patient (30) from an authorized third party, such as a pharmacy, medical device manufacturer, or other provider of such devices. Accordingly, the ocular imaging unit (40) can be positioned at the location of the patient (30), and specifically, in the patient's home.

When prescribed, the ocular imaging unit (40) may be loaded with information specific to that particular patient (30). This can include identity information, such as age and sex, physical characteristics, such as interpupillary distance, and/or existing medical conditions or prior medical diagnoses.

The ocular imaging unit (40) is connected to a personal computing device (50) for the control and/or transmission of data to and from the unit (40) The personal computing device can be any computing device commonly found in the home and capable of communicating information to a remote location to and from the Internet, whether via hardwired connections (e.g., Ethernet, coaxial cable, etc.) or wirelessly (e.g., via cellular data technology). Such personal computing devices include desktop computers, portable computers (such as laptops, notebooks, and netbooks), tablets, smartphones, smartwatches, and similar smart devices.

The ocular imaging unit (40) has either a hardwired connection (e.g., USB) to a personal computing device (50), or a wireless connection to a personal computing device (54). The wireless connection will typically be achieved via connecting both the imaging unit (40) and the computing device (54) to the same WiFi network. However, when required (such as homes without an available WiFi network), and depending on the data transmission requirements, other wireless technologies, such as, for example, Bluetooth, may be employed to enable communication between the imaging unit (40) and the computing device (54).

Once a physician determines that a particular patient (30) presents an actual or potential risk of disease or disfunction of the ocular anatomy, the physician prescribes the ocular imaging unit (40) to that patient, as described above. Once the ocular imaging unit (40) is obtained by the patient (30), it can be used by the same, or a different physician, in order to monitor the ocular anatomy of the patent (30). For example, on occasion, a patient's general physician may determine at an annual physical that the patient is at risk of ocular disease or disfunction, and then prescribe the ocular imaging unit (40) for subsequent monitoring by an optometrist.

Once the patient has obtained the ocular imaging unit (40), it can be used to enable the relevant physician (60) to remotely monitor the ocular anatomy of the patient (30). As a result, the physician (60) is able to ensure that the health of that ocular anatomy does not worsen or, if it does, that any such worsening is attended to urgently.

Specifically, rather than requiring the physician (60) to perform a full examination and make a medical diagnosis, the ocular imaging unit (40) can be used to initiate a remote, pre-diagnostic evaluation by the physician (60). As a result, the physician (60), upon receiving an alert from the unit (40), uses a personal computing device (70) at the physician's remote location to perform an initial assessment of the patient's ocular anatomy, without making a medical diagnosis, in order to determine whether a full examination is warranted. The personal computing device (70) may be, for example, a personal computer, but may also be any other device capable of displaying images of the patient's ocular anatomy obtained by the imaging unit (40) and transmitted by the patient's personal computing device (50) over a network (80)—i.e., the Internet.

If, after remotely performing a pre-diagnostic evaluation, the remote physician (60) determines that a full medical examination is required, the physician (60) can use the system (20) to communicate an instruction to the patient (30) accordingly.

In some cases, the system (20) also includes a server (90) that communicates over the network (80) with both the patient's computing device (50) and the physician's computing device (70). In instances where the physician (60) is not immediately available to review imaging of the patient's ocular anatomy at the time it is captured by the ocular imaging unit (40), the imaging data can be communicated from the patient's computing device (50) to the server (90) and stored thereon, such that the imaging data can later be accessed by the physician's computing device (70) in order to perform the pre-diagnostic evaluation.

The communications between the devices over the network (80) are HL7 compliant so that the information remains secure.

Figure 2A:
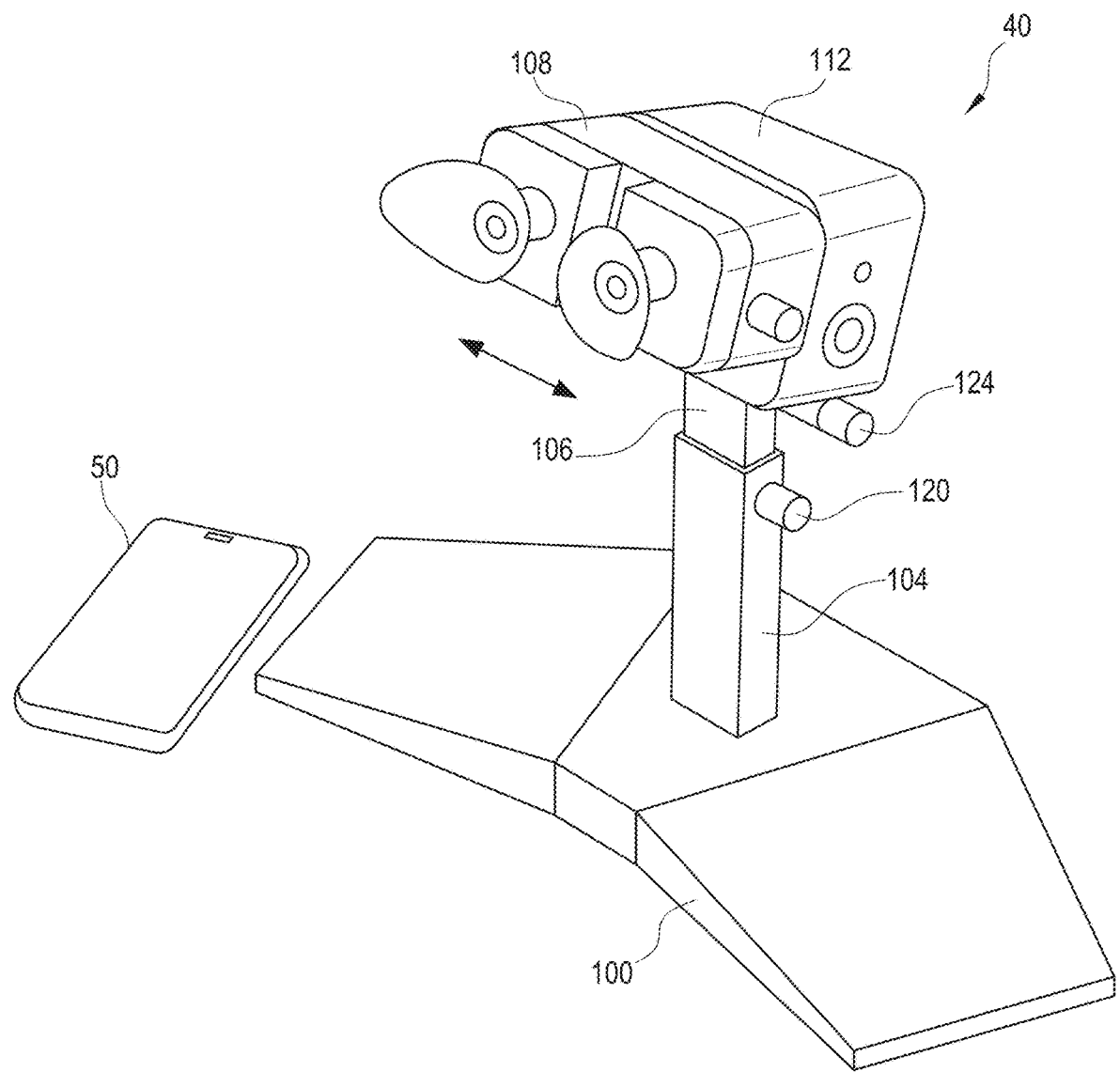
FIG. 2A is a perspective view of the home ocular imaging unit of FIG. 1.
Figure 2B:
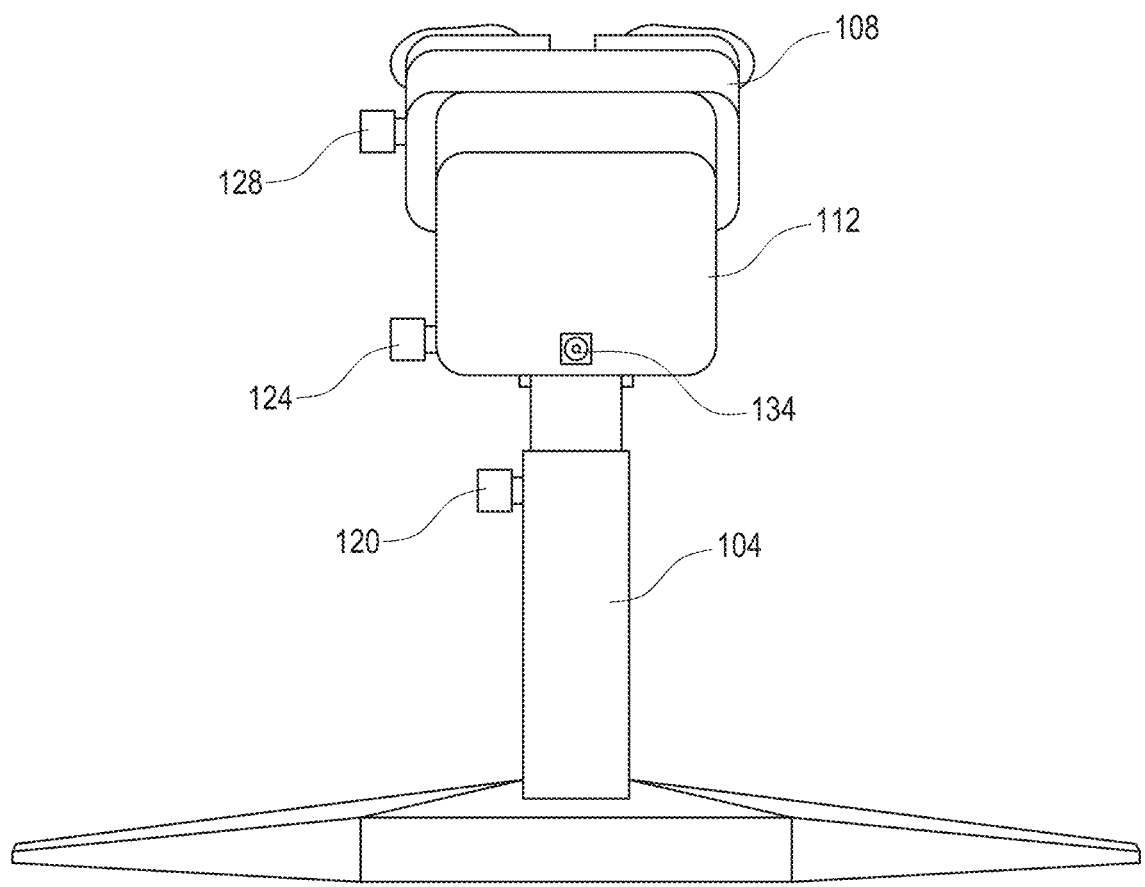
FIG. 2B is a rear view of the ocular imaging unit of FIG. 2B.
Figure 2C:
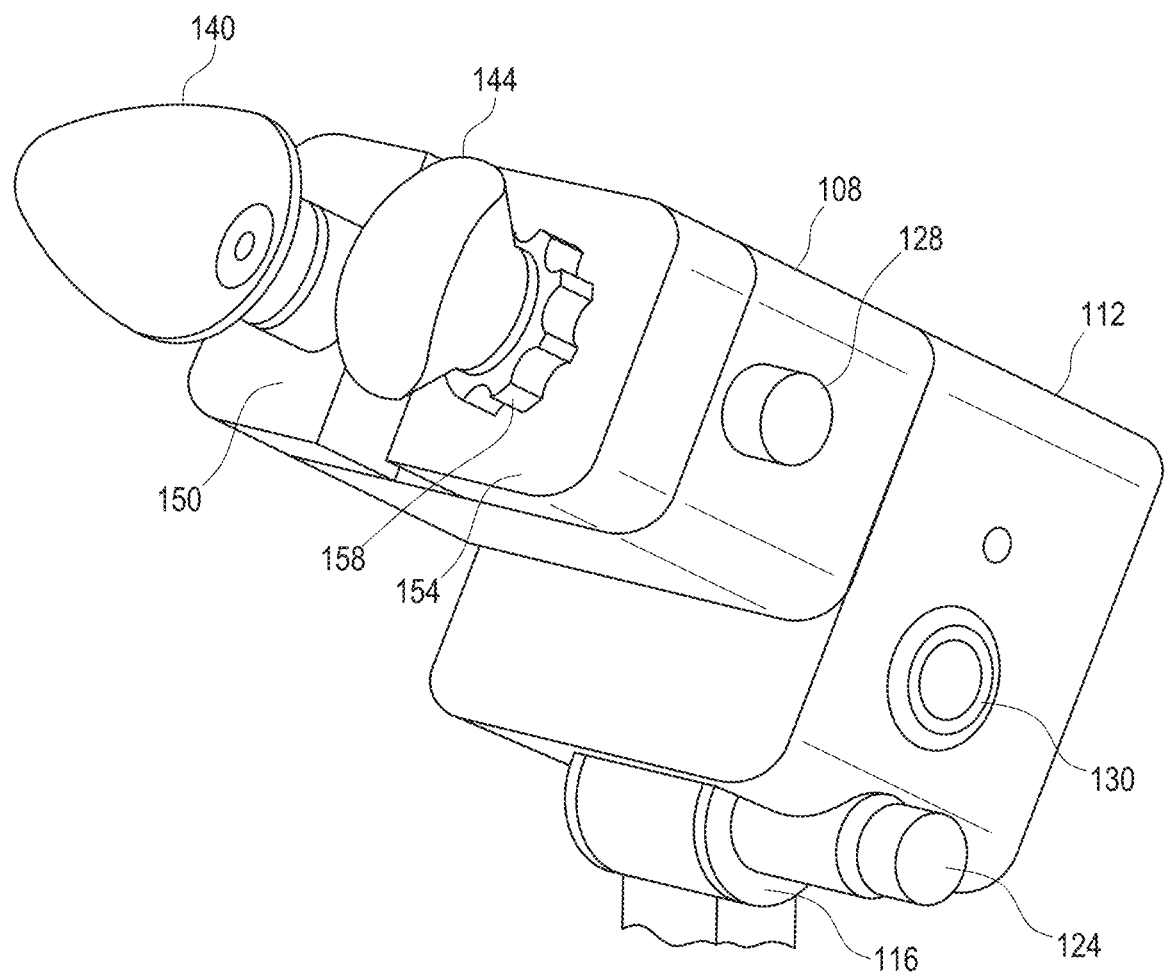
FIG. 2C is a perspective view of the front and rear portions of the ocular imaging unit of FIG. 2C.
Figure 3:
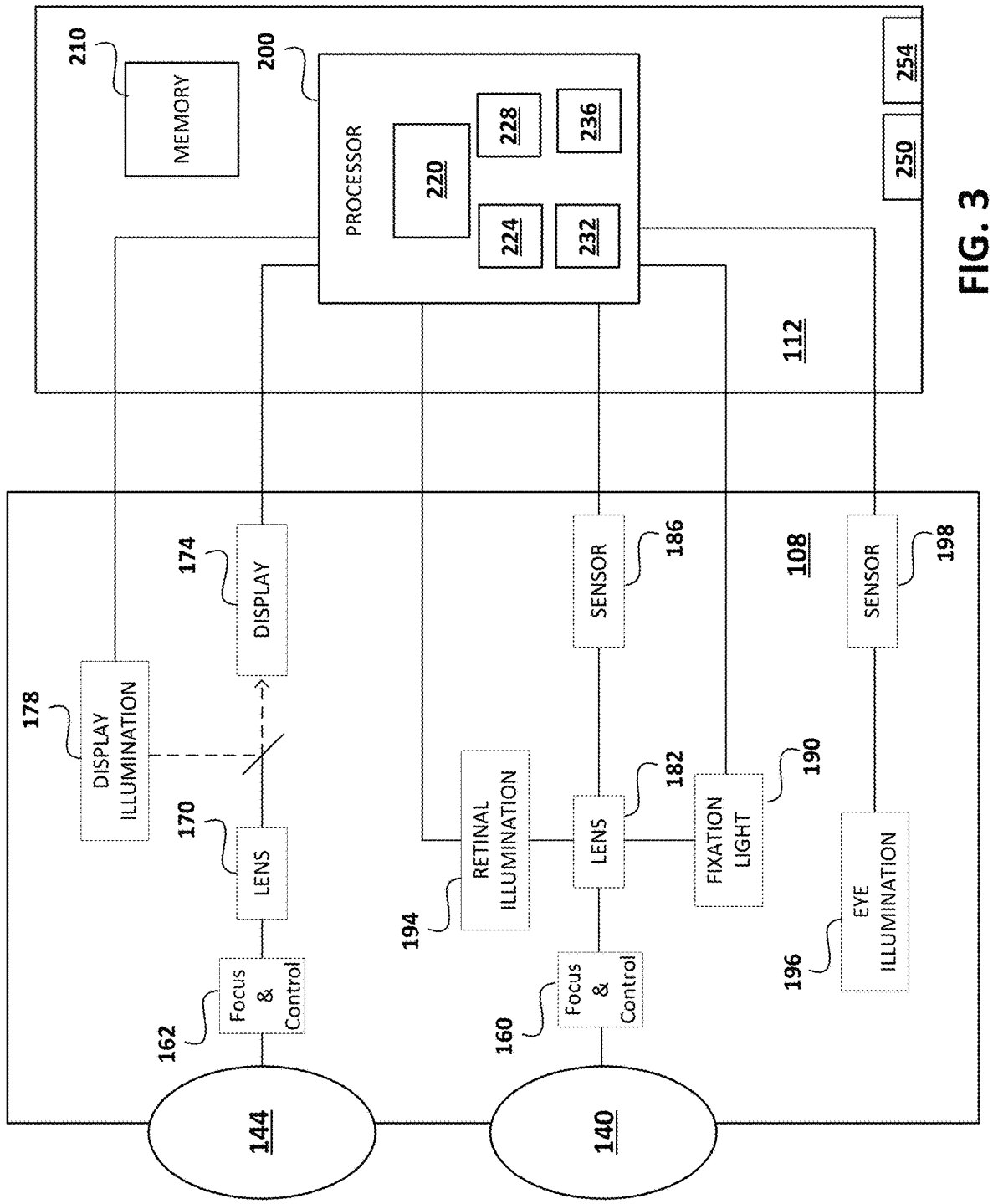
FIG. 3 is a schematic view of the basic components of the front and rear portions of the ocular imaging unit of FIG. 2C.

Referring to FIGS. 2-3, the basic components of the ocular imaging unit (40) are depicted. As shown in FIG. 2A, the ocular unit includes a base (100), a vertical support (104), a first, front portion (108), and a second rear portion (112). The front portion (108) performs the various imaging functions of the unit, while the rear portion (112) performs the various processing functions of the unit, as shown schematically in FIG. 3 and further described below.

The ocular imaging unit is connected to a power source (not shown), and includes a power button (not shown) for turning the device on and off. Accordingly, as shown in FIG.

2B, the rear portion (112) includes a connection (134) for a power cord. However, it should be noted that battery power may also be employed, either as a primary or backup source of power.

The ocular imaging unit (40) is highly adjustable in order to accommodate the requirements of the particular patient using it. Accordingly, the vertical support (104) includes a telescopic member (106) that extends out of the portion connected to the base (100), which can be locked in place by tightening a knob (120), such that the height of the upper portions (108, 112) can be adjusted. Additionally, the rear processing portion (112) is connected to the vertical support (104) by a hinge joint (116), which can be locked in place by tightening a knob (124), such that the upper portions (108, 112) can be pivoted relative to the vertical support (104) in order to obtain the appropriate tilt angle.

The ocular imaging unit (40) is also adjustable in order to facilitate different types of evaluations. Referring in particular to FIG. 2C, the front imaging portion (108) includes a first eye cup (140) and a second eye cup (144), which are used to evaluate the ocular anatomy in different ways in a non-contact manner. By using eye cups, the eyes are shielded from ambient light that might otherwise interfere with the artificial illumination of the device or otherwise affect the eye so as to impact the evaluation being performed. Further, when one eye is illuminated, the other remains in the dark.

In order to be able to use both eye cups (140,144) on the same eye, the front imaging portion (108) is rotatable 180 degrees relative to the rear imaging portion (112) in order to allow both of the eye cups (140, 144) to be used on each individual eye. Once disengaged from its current position and rotated 180 degrees, the imaging portion will click into the new position to prevent undesirable movement during the subsequent evaluation.

The front imaging portion (108), which includes the relevant optics, sensor, and display, includes first and second moveable imaging sections (150, 154), which further include the first and second eye cups (140, 144), respectively. The first and second imaging sections (150, 154) are slidable relative to each other, such that they can be adjusted for the specific interpupillary distance of the particular patient using the unit. In order to achieve precise positioning when sliding the imaging sections (150, 154), this adjustment can be accomplished with a knob (128). Additionally, a dial (158) is provided adjacent one or both of the eye cups (140, 144) for adjusting focus and accommodation.

As shown in FIG. 3, the eye cups (140, 144) may be used for two different optical paths. The first eye cup (140) is used for an imaging path, wherein the ocular imaging unit (40) images the patient's eye—namely, retinal imaging and/or imaging of the eye exterior. The second eye cup (144), on the other hand, can be used for a testing path, wherein the physician and/or the ocular imaging unit (140) audibly guides the patient through visual tests.

With respect to the first eye cup (140), the patient looks though a lens (182), towards an image sensor (186). For Instance, the sensor (186) may be a complimentary metal oxide semiconductor (CMOS) sensor, such as, for example, a high definition (2588×1520 pixels), high sensitivity (32,000 e-/lux sec), high dynamic range (40.6 db) CMOS sensor. In other exemplary embodiments, the sensor may be a CCD, such as, for example, a diagonal 11 mm (Type 2/3) interline CCD sensor with a square pixel array with 5.07 M effective pixels and a frame readout of approximately 1/3.75 second.

Auto focus and auto accommodation (160) is also provided in order to make adjustments for the particular patient who is doing the viewing.

A fixation light (190) is used to align the eye with the optical axis. For example, a red LED light can be projected with a half mirror into the optical path, and the patient can be instructed to focus on the red light. In some embodiments, a display (192) is employed for this purpose.

Once the eye is fixated, an illumination source (194) is used to illuminate the retina in order to capture one or more images thereof. When the eye is in the dark (i.e., shielded from any ambient light by the eye cup), the iris opens. The illumination source (194) can generate a flash to capture an image of the retina while the iris is still open, for example, by pulsing a white LED, and thereby obtain a full color image.

Alternatively, the illumination source (194) can illuminate the retina with near infrared light. Because the iris does not react to near infrared light, real time images/video can be obtained. Though the resulting images will be monochromatic, this can nevertheless be useful, for example, for imaging the arteries. The fixation light (190) can likewise be near infrared.

In certain embodiments, the first eye cup (140) can also be used to capture images of the exterior of the eye. In this case, the illumination (196) may comprise, for example, an LED ring around the inside of the eye cup (140). For example, simultaneously with or shortly after fixation, the illumination can be gradually increased while the pupil size is measured.

Figure 4A:
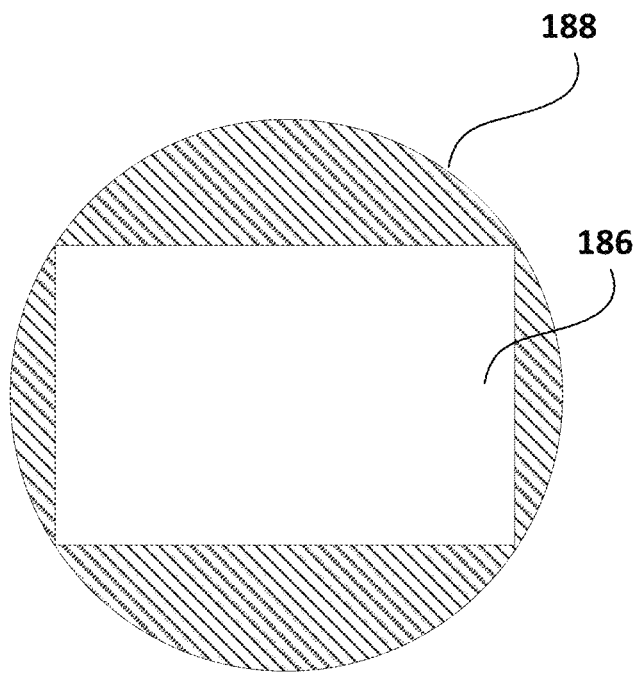
FIG. 4A is an end view of the image sensor of FIG. 3 within the optical image produced by the ocular imaging unit.
Figure 4B:
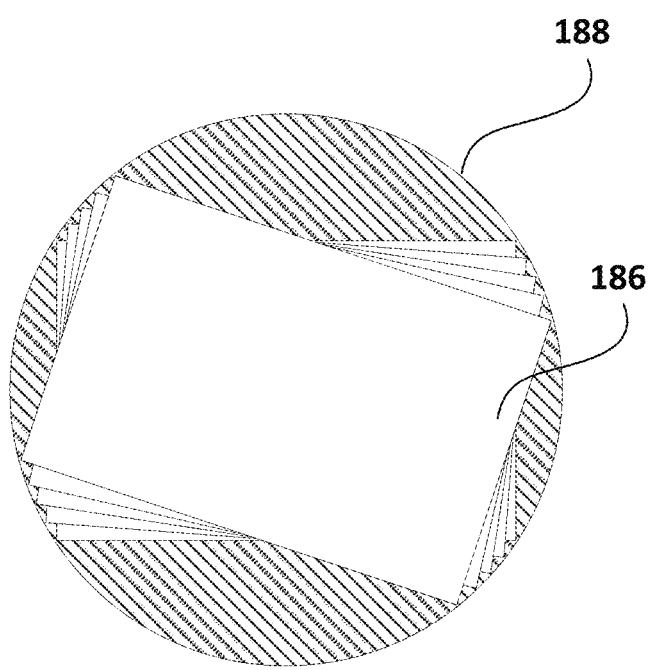
FIG. 4B is an end view illustrating the rotation of the sensor of FIG. 4A within the optical image.

The sensor (186) is typically rectangular, and in some cases, is square. As a result, as shown in FIG. 4A, the sensor (186) does not typically capture the full field of view of the optical image (188). Therefore, as shown in FIG. 4B, the sensor (186) can be rotated 180 degrees, for instance with a stepper motor in one-degree (or other appropriate) intervals, to capture a sequence of images that can then be stitched together. In this way, the ocular imaging unit (40) is able to obtain a fuller visible field of view.

Figure 5A:
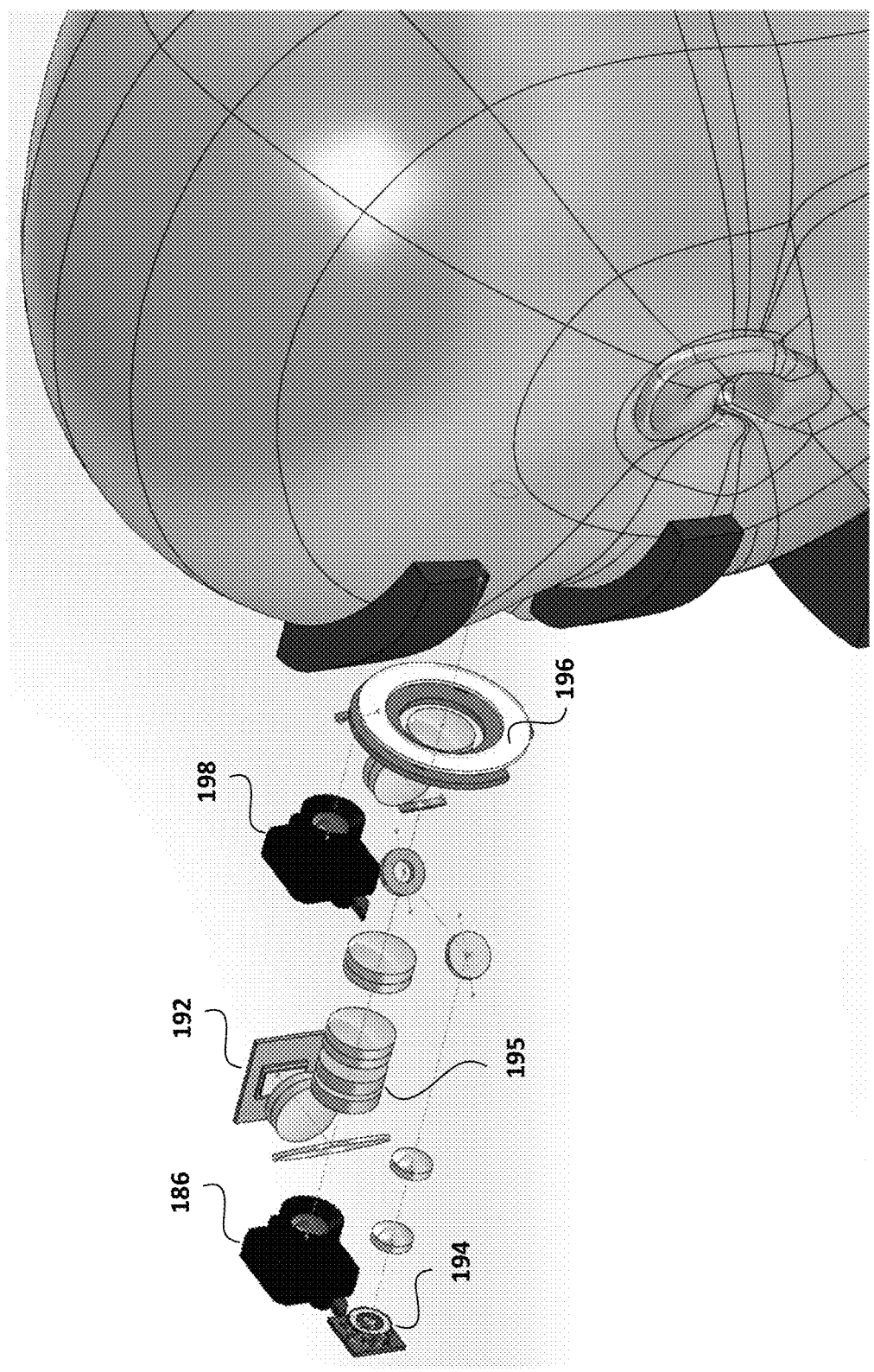
FIG. 5A is a perspective view of the imaging optical assembly of FIG. 3.
Figure 5B:
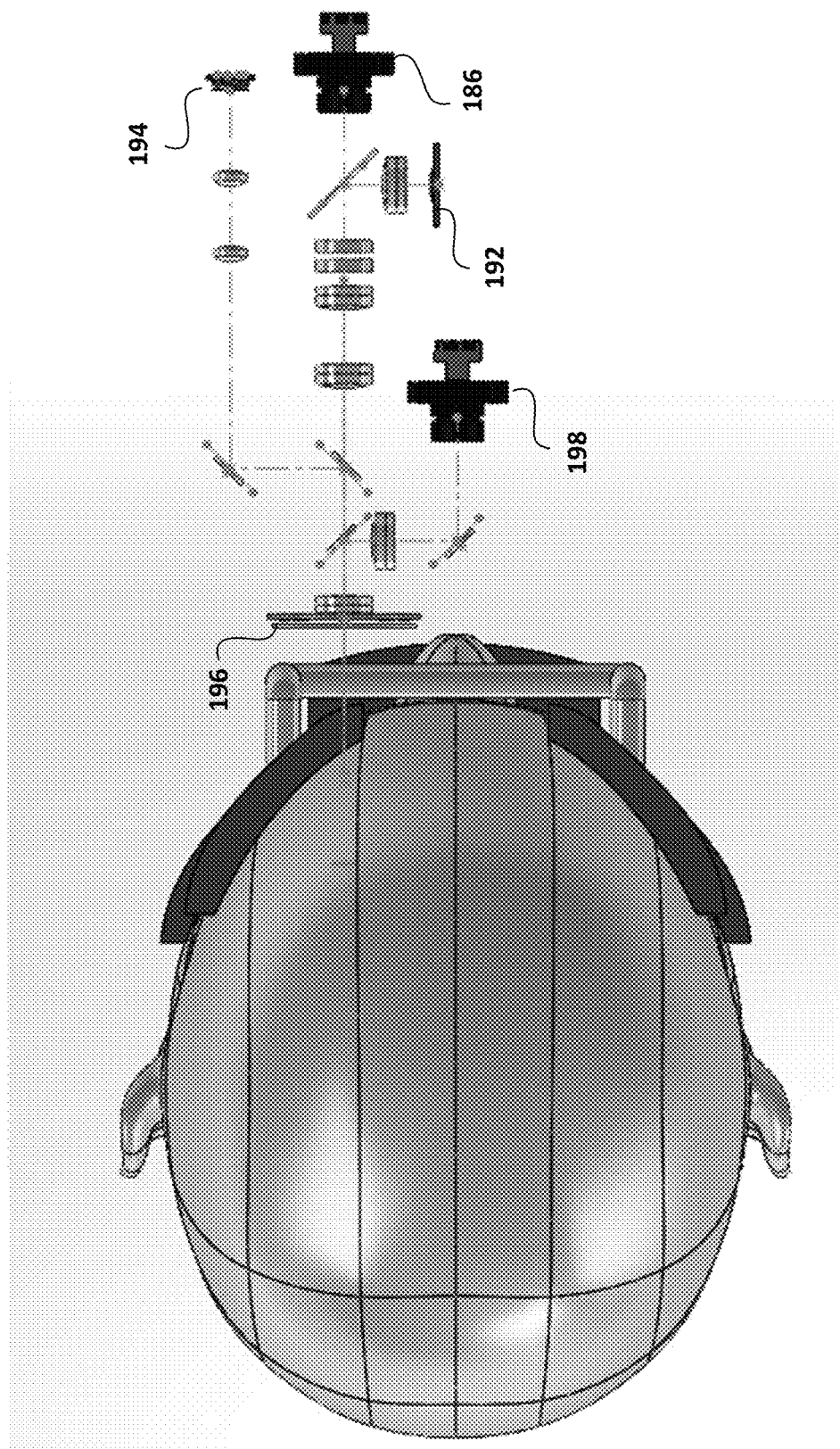
FIG. 5B is a top view of the imaging optical assembly of FIG. 5A.
Figure 5C:
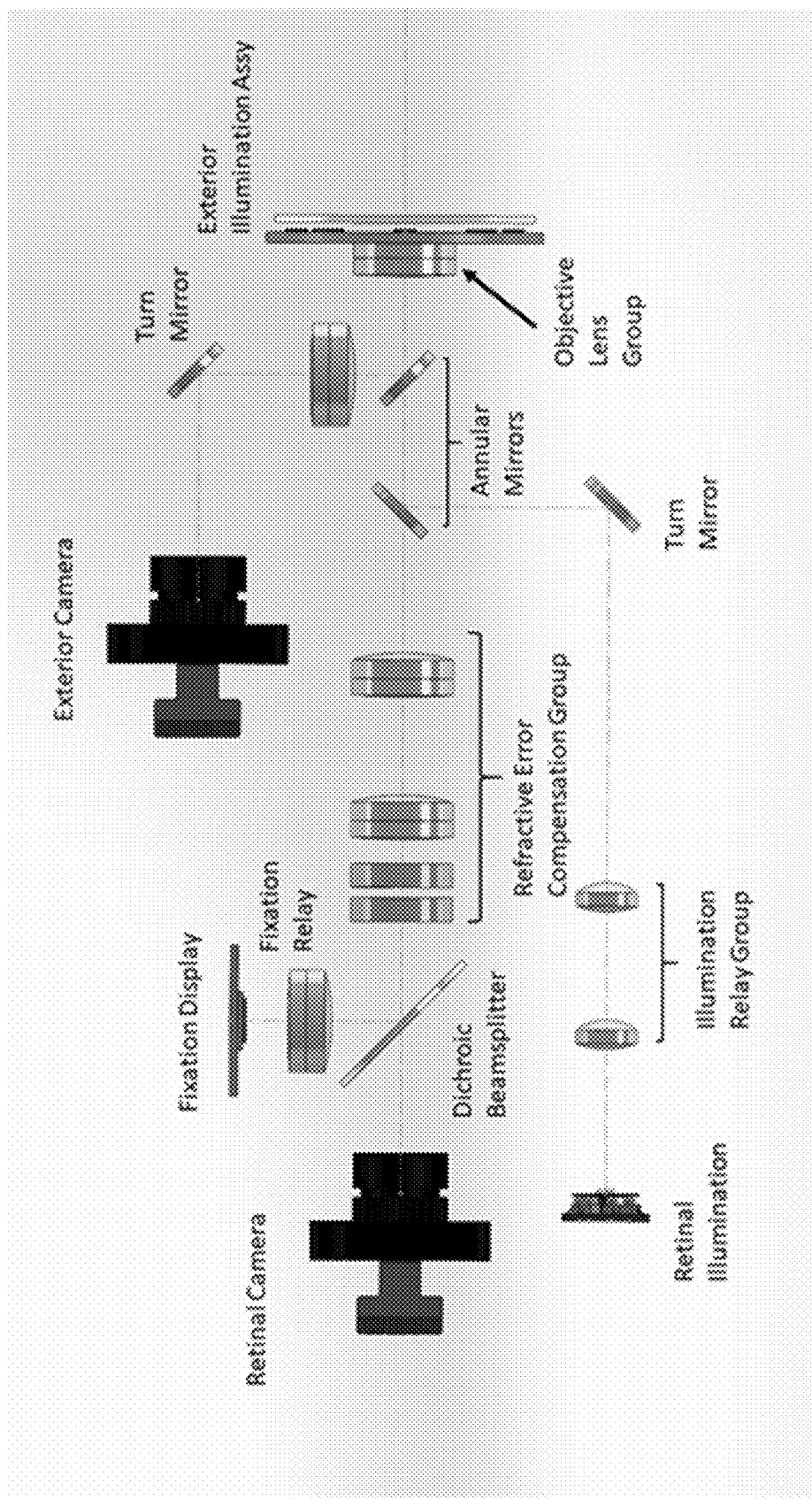
FIG. 5C is a detailed schematic of the optical elements of FIG. 5B.

An exemplary embodiment of the above described optical assemblies, including the relevant lenses, illumination sources, reflectors, and sensors, is illustrated in FIGS. 5A-C. Additionally, optical elements (195) for refraction error correction are also provided. It should be noted, however, that any other suitable arrangement of optical components may be employed.

Returning to FIG. 3, the second eye cup (144) may be used with several different kinds of imaging sections. For example, in certain embodiments, the second eye cup and imaging section (144, 154) may be the same type of assembly as the first eye cup and imaging section (140, 150). In these cases, the above described rotation of the front imaging portion (108) is unnecessary.

In other embodiments, the second eye cup and imaging section (144, 154) may include the above-described illumination and optics for imaging the exterior of the eye, resulting in a dedicated imaging section and sensor separate from the imaging section used for retinal imaging.

Finally, in certain embodiments, the second eye cup and imaging section (144, 154) may be used for conducting tests. As noted above, in the event that the physician's remote pre-diagnostic evaluation determines that an in-person diagnostic examination is required, the physician can perform and initial diagnostic tests remotely.

In such an exemplary embodiment, the patient looks through a lens (170) to view a display (174), such as a liquid crystal on silicon (LCOS) microdisplay. A processor (200) in the rear processing portion (112) communicates to an illumination source (178) a particular test pattern to be displayed, and the output of the source (178) is reflected onto the display (174) to create a virtual image for the eye to focus on during testing. This virtual image may, for example, appear to the patient to be an image that is 40 inches diagonally and three feet away. These test patterns are appropriately scaled based on the size and distance of the virtual image. The patient is then asked to respond to various aspects of his/her visualization of the test pattern.

The rear section (112) includes the processor (200) referenced above, which may include one or more large scale integration (LSI) components such as a field programmable gate array (FPGA), and performs major processing and functions for the ocular imaging unit (40). The rear section also includes any memory (210).

In particular, the processor (200) includes a microprocessor (220), which controls all internal units and communicates with the connected personal computing device (50).

The processor (200) also includes a camera control unit (224), which attends to communication with the sensor, sensor register settings, white balance, gain, brightness, sharpness, exposure, black balance, power levels, etc.

The processor (200) also includes an illumination control unit (228), which turns the various illumination sources on and off and sets appropriate power levels for the desired intensities.

The processor (200) also image processor unit (232), which receives images from the sensor (186), captures the images, processes the images, makes measurements, and transmits the images to the personal computing device (50). The image processing includes functions such as capturing a video frame in temporary memory, transferring a frame to processing memory, making measurements, conducting operations to correct for uneven illumination, conducting various distortion correction operations, conducting various enhancement operations (sharpness, edge detection, color corrections, including various color views), and conducting operations involving multiple images (stitching, combining, S/N improvements).

The processor (200) also includes a motor control unit (236), which controls the various actuators (motors, piezoelectric drives, etc.) based on commands received from the microprocessor (220). For example, while the various types of mechanical adjustments of the unit (40) may be accomplished by manually manipulating knobs (120, 124, 128), these adjustments may also be executed via servomechanisms controlled by the processor (200).

In some embodiments, the processor (200) includes pre-programmed calibration data. This can take various forms.

For example, in some cases, the ocular imaging unit (40) may be used by several patients in the same home. These different users may have different height and tilt requirements for the device, and preferences for these separate individuals can be pre-stored. Then, when a particular patient logs in, the processor may issue an alarm that the settings are wrong for that particular patient, or it may adjust the settings automatically with servomechanisms controlled by the processor (200). Likewise, patient-specific physiological reference data may also be stored, such as the size of a retinal blood vessel, which can then be used as a baseline for that patient.

The preprogrammed calibration data may also relate to image processing. For example, in exemplary embodiments, the ocular imaging unit performs illumination correction for the captured images. When the appropriate data is preprogrammed, such as illumination type and sensor pixel distance, the processor can then perform illumination correction by adjusting the intensity of the light received by the individual sensor pixels.

The processing section (112) also processes various kinds of audio commands and communications, including both those that the ocular imaging unit (40) issues to the patient (30) and those that it receives from the patient (30). For this purpose, the ocular imaging unit may include its own microphone (250) and/or speaker (254) to receive and produce this audio, or it may use the microphone/speaker of the personal computing device (50) connected to the unit (40).

For example, if the patient is experiencing an ocular emergency and would therefore have difficulty viewing the screen on his/her smartphone (50), the patient may desire to initiate an evaluation and send an alert to the physician with an oral command instead.

As another example, the imaging unit (40) may issue audio instructions to the patient (30) during the course of a particular evaluation because the patient will not be able to read written instructions while his/her eye is being imaged. For the same reason, the unit will receive and process verbal confirmations from the patient (30) that he/she has completed a given step of the procedure so that the imaging unit (40) knows it is time to capture an image/video or move to the next step. The unit may also need to obtain verbal feedback from the patient (30) regarding what he/she sees during the procedure to that it can communicate this to the physician (60).

Figure 6:
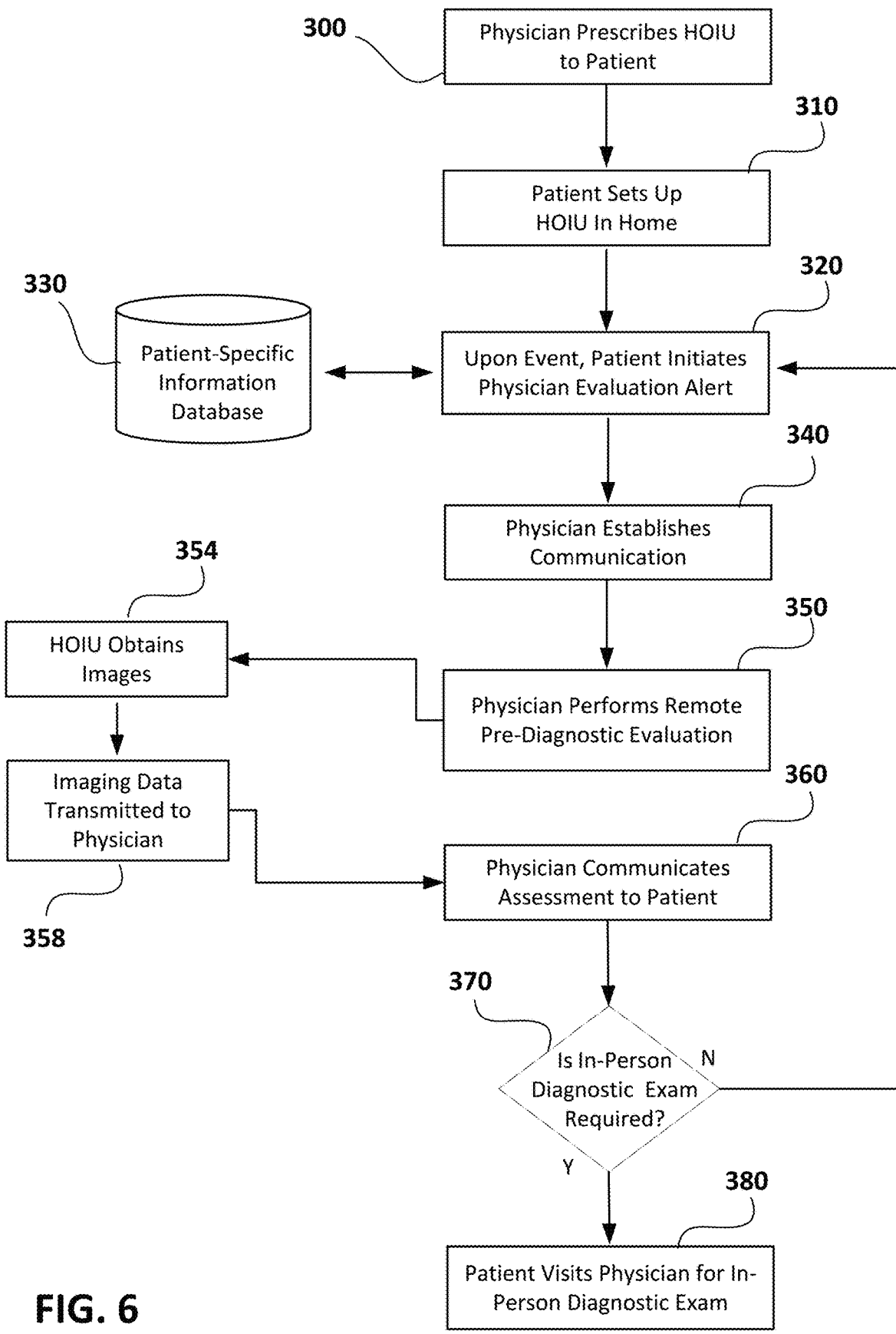
FIG. 6 is a flow chart illustrating the basic operation of the system of FIG. 1.

Referring to FIG. 6, the general operation of an exemplary embodiment of the system (20) is shown. When a physician determines that a patient is at-risk, either for a strictly ocular condition or for a condition with which ocular pathologies are associated, the physician prescribes (300) a home ocular imaging unit (such as the exemplary embodiment illustrated in FIGS. 2A-C) to the patient. The patient may use the prescription to obtain the home ocular imaging unit from a pharmacy or the manufacturer, or in some cases, may receive it directly from the physician.

Once the patient obtains the home ocular imaging unit, the patient sets up (310) the imaging unit at a location in their home where he/she will be able to comfortably utilize the device to image his/her eyes and where the unit can establish a connection with a network over which images can be communicated to the physician. As noted above, this may be via a hardwired or wireless connection to a home network connected to the Internet, but may also be via cellular data technology.

The home ocular imaging unit will typically be connected to a personal computing device such as a smartphone, but in certain embodiments, the ocular imaging unit itself may directly connect to the relevant network without the use of an intermediary personal computing device. When connected to a smartphone, this connection between the unit and the phone will typically be wireless. However, in some cases, the smartphone can be plugged into the imaging unit, for example, via a USB cable.

Figure 7B:
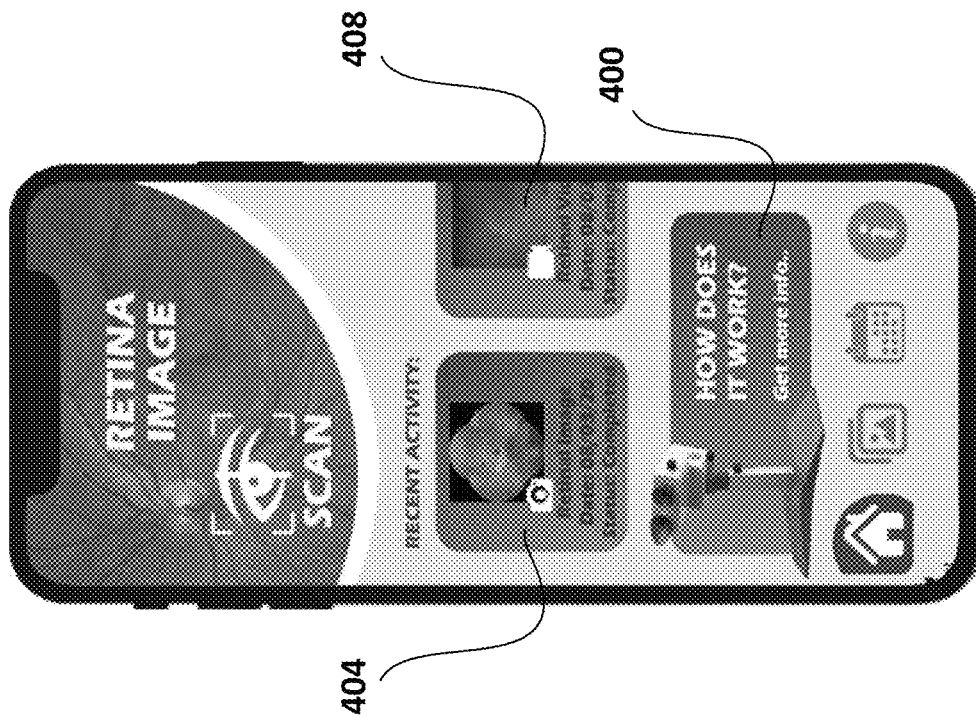
FIG. 7B is an image of a home screen for the smartphone application of FIG. 7A.
Figure 7A:
FIG. 7A is an image of a patient login screen for a smartphone application for using the system of FIG. 1.

Once connected to the smartphone, the patient can open an app designed to work with the home ocular imaging unit, as shown in FIG. 7A. Upon opening the app, the patient will be presented with a screen for logging into their personal account.

An example home screen that the patient may see upon logging in is shown in FIG. 7B. The format of the main screen may vary and, in some embodiments, even be customizable by the patient or physician. In the exemplary embodiment shown, various links for basic features are provided, such as information on how to operate the device (400), a scrolling menu of previously recorded still images and videos (404, 408), and other basic functionality, such as initiating a new image acquisition session, calendaring, and accessing additional information.

Figure 8B:
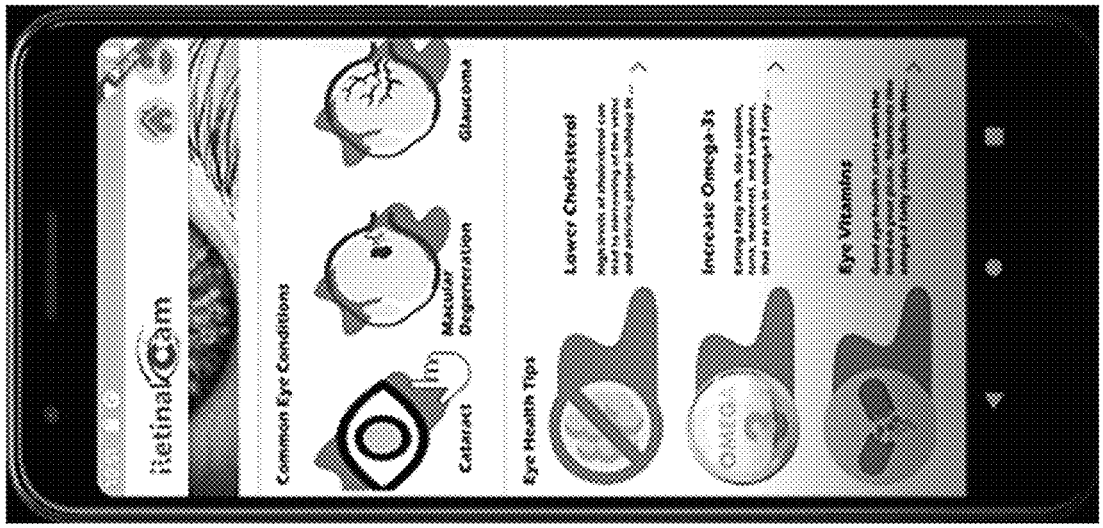
FIGS. 8A-D are images of information screens of the smartphone application of FIG. 7A.
Figure 8A:
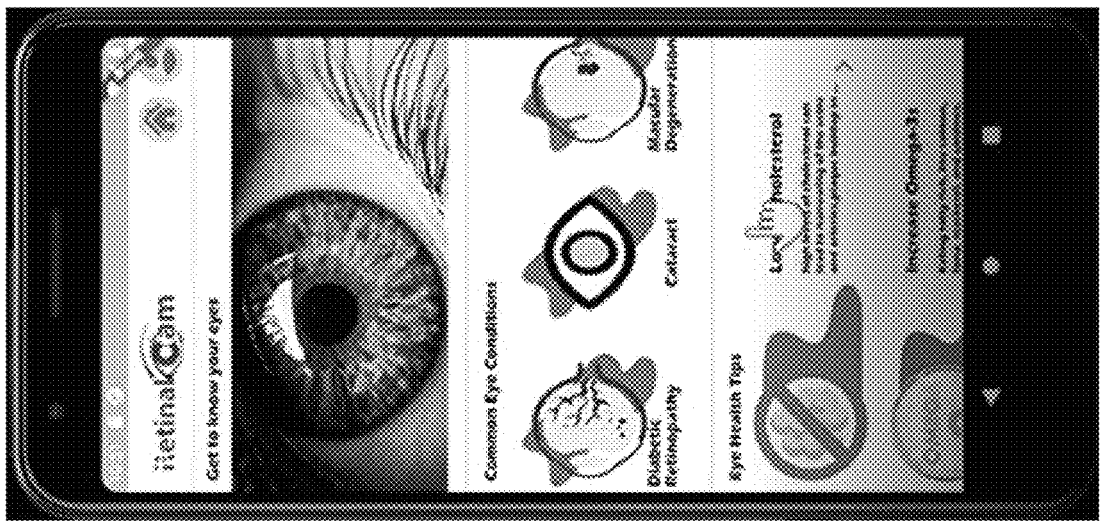

In exemplary embodiments, the app includes an informational section, shown more fully in FIGS. 8A-D. Referring first to FIGS. 8A-B, in this particular example, the patient may select "Get to know your eyes," in which the patient can read information regarding eye composition, parts of the eye, etc. The patient can also scroll through a selection of "common eye conditions" to find a particular condition of interest, as well as a series of "eye health tips." Because the patient may be experiencing visual impairments when seeking this information, the options and the information may be read audibly to the patient, and likewise, the patient can make selections using verbal commands.

Figure 8D:
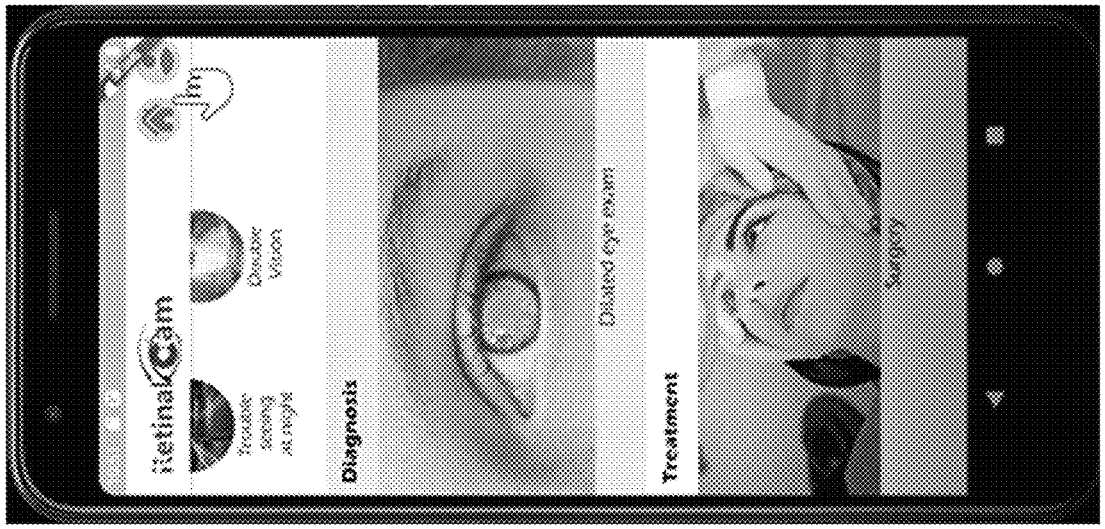
Figure 8C:
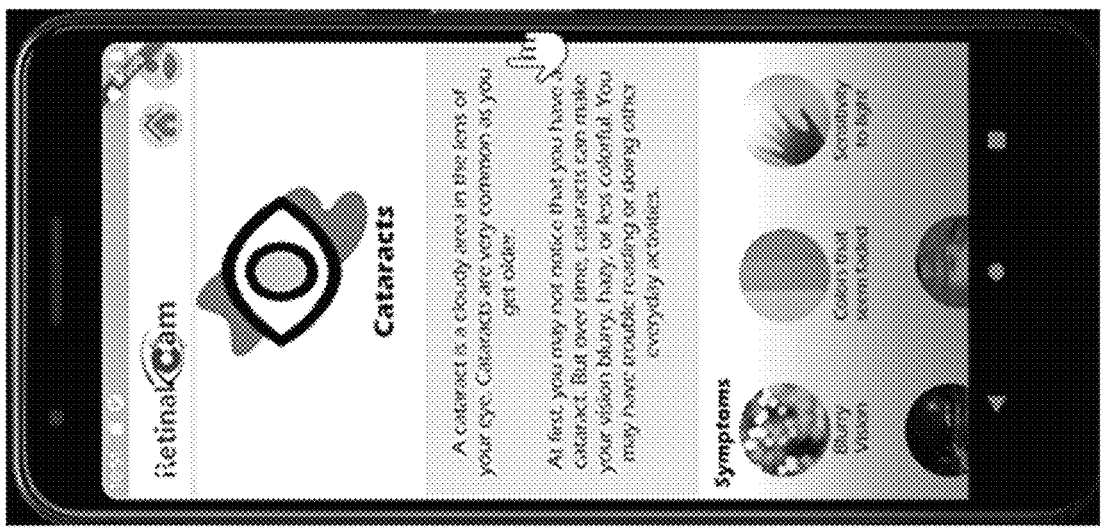

As shown more fully in FIGS. 8C-D, by selecting a particular eye condition (e.g., cataracts), the patient can review a lot of additional information to become more educated. This can include common symptoms, how the condition is diagnosed, and what treatment may involve.

Returning to FIG. 6, once logged in, the patient can initiate (320) a physician alert. Typically, this will be when the patient either experiences or observes an adverse event, such as blurriness, pain, red spots, etc. However, it should be noted that, for certain high-risk patients, these physician alerts may be initiated according to a particular schedule prescribed by the physician. Additionally, the physician can prescribe a particular regimen of tests to be performed offline by the patient, stored in the memory of the ocular imaging unit or smartphone, and transmitted to the remote physician or remote server (90), and the physician then receives an alert when this imaging data is received by the physician's computing device (70) or is available for access on the server (90).

The patient may initiate the alert by making this selection on the screen of their connected smartphone (50). However, because the patient will sometimes have trouble viewing the screen due to the current ocular condition he/she is experiencing, the patient can initiate the physician alert with an audible command, which can be received by the microphone of the ocular imaging unit or the smartphone in communication therewith.

Once logged in, information specific to the patient may be retrieved from a database (330). As noted above, this data will include not only the patient's identity, but can also include various types of information associated with that patient. For example, it may include general demographic information, such as age, race, gender, employment, etc., which could have some bearing on the state of one's ocular health. It may also include certain relevant physical characteristics of the patient's ocular anatomy, such as eye color, iris diameter, interpupillary distance, etc. It may also include existing medical conditions related to ocular pathologies or potential ocular pathologies, such as diabetes, arthritis, Alzheimer's, etc. Finally, this information may include prior diagnoses and/or imaging of the ocular anatomy for reference and comparison by the physician.

Using the patient's login credentials, this patient-specific data will typically be retrieved from a remote server (90) where data for all such patients is stored. However, in some cases, this data is stored in the memory (210) of the ocular imaging unit itself.

At the time the system transmits the physician alert to the physician with the patient-specific data, images (a still image, a sequence of still images, or a video) can also be sent along with the alert for an initial preliminary view of the eye prior to the physician conducting the remote pre-diagnostic evaluation described below. The images may comprise an ordinary photo or video taken by the patient with the smartphone itself, or they may comprise more sophisticated imaging captured by the patient with the ocular imaging unit, as is further described below.

This imaging sent with the physician alert may help the physician to determine the urgency with which he/she needs to conduct the pre-diagnostic evaluation. For example, if the doctor is on the road and the only computing device he/she has is a smartphone on which the alert was received, a quick look at a photo of the eye may indicate whether the physician should hurry to a nearby computer that will enable better remote viewing of the patient's ocular anatomy.

When the physician receives the alert, the physician establishes communication (340) with the patient over the network. Once communication is established, the physician can perform the remote, pre-diagnostic evaluation in several ways.

The physician will issue instructions to patient over the network to perform certain tasks while the physician conducts the pre-diagnostic evaluation, such as instructing the patient to look though an eye cup, to focus on a fixation light, or to articulate what the patient sees when looking at a test pattern.

While guiding the patient along with these instructions, the physician will typically remotely control the ocular imaging unit for the purpose of displaying desired test patterns, capturing images, and the like. The physician does this by issuing commands via manual input or verbal statements using the physician's personal computing device, and these commands are then transmitted over the network to the ocular imaging unit in the patient's home.

In some instances, however, the physician may simply instruct the patient to perform these actions. In these cases, for example, an image capture command is input by the patient, usually with a verbal command because the patient will be looking though the eyecups of the ocular imaging unit while issuing the command. However, as illustrated in FIG. 2C, an easy access button (130) may also be employed for basic functions (e.g., capturing an image), or for providing a confirmation (e.g., answering a query from the unit, such as "do you see the red dot?").

In exemplary embodiments, the ocular imaging unit is used not only for imaging of the ocular anatomy, but also for visual tests.

As previously noted, the first imaging section (150) includes an appropriate lens, illumination sources, and image sensor for capturing images of the retina. The first imaging section (150) is used to capture (354) one or more images of the patient's ocular anatomy in the form of a single still image, a sequence of separate still images, a recorded video, or a live video stream from the patient's location to the physician's location. The imaging data is then transmitted (358) to the physician, and the physician can use these images to remotely assess the likelihood of various eye pathologies, such as, for example, diabetic retinopathy, diabetic maculopathy, macular degeneration, optic neuritis, retinal vasculitis, retinal detachment, and retinitis pigmentosa.

In certain embodiments, the physician can also use this first imaging section (150) to capture images of the exterior of the eye, enabling the doctor to obtain a preliminary indication of anything from the presence of a sty to conjunctivitis to amblyopia.

In some embodiments, the processor (200) derives measurement data (such as pupil size, blood vessel diameter, etc.) from these captured images. This measurement data can then be transmitted to the physician, simultaneously with or subsequent to the transmission of the imaging data.

The above-described versatile ocular imaging unit allows the physician's pre-diagnostic evaluation (350) to include a preliminary evaluation of various parts of the eye, including the vitreous media, retina, retinal vessels, optic nerve, and macula. As a result of these various testing and imaging capabilities that the physician can use remotely, the physician is able to make a preliminary assessment about a myriad of eye conditions that could potentially lead to blindness, vascular disorders (such as diabetes, hypertension, and stroke), and neurological disorders.

After the physician performs the pre-diagnostic evaluation (350), the physician then communicates (360) his or her assessment regarding whether an in-person diagnostic examination is necessary. If it is, the patient schedules and attends a visit (380) with the physician or appropriate eye specialist so that a full, diagnostic examination can be performed. If an in-person diagnostic examination is not required, the patient returns to a state of self-monitoring, and initiates a new physician alert (320) upon the occurrence of the next adverse event.

Additionally, in some cases where the pre-diagnostic evaluation indicates it is warranted, the physician then uses the ocular imaging unit to perform an initial diagnostic evaluation remotely.

Specifically, as described above, in some embodiments, a second imaging section (154) includes a display and corresponding illumination source for presenting virtual images to a user. The physician can use this second imaging section to display any one of various types of test patterns designed to test for various kinds of visual impairments. These test charts can be downloaded by the physician (or at the instruction of the physician) as needed.

Figure 9D:
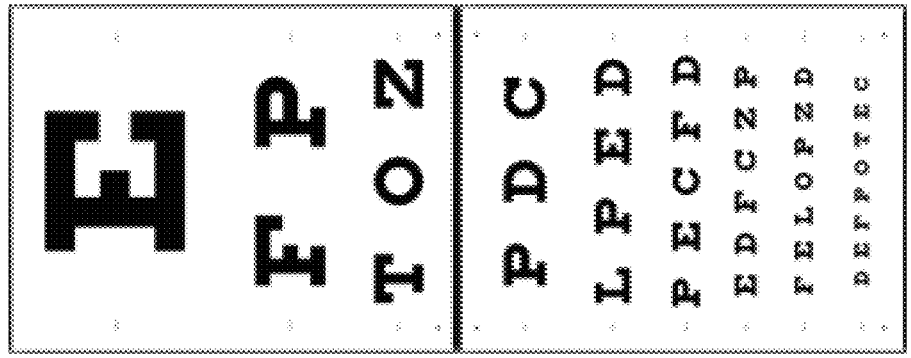
FIG. 9D is a view of a visual acuity chart.
Figure 9B:
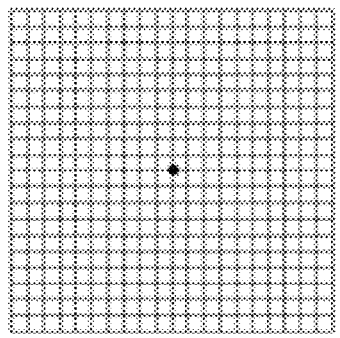
FIGS. 9B-C are views of an Amsler grid.
Figure 9C:
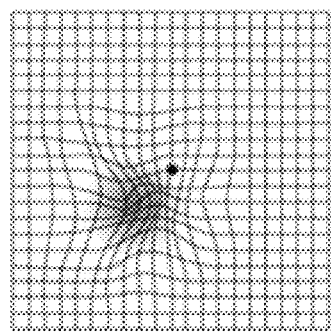
Figure 9A:
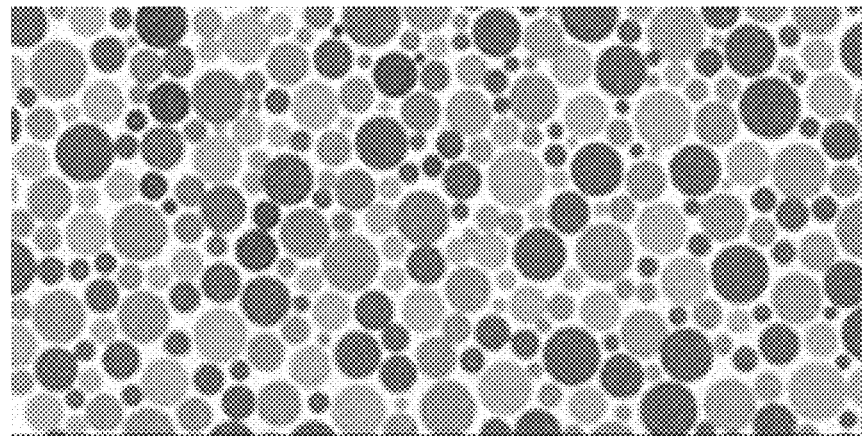
FIG. 9A is a view of a display pattern for a colorblindness test.

For example, one type of pattern that may be displayed is a pattern used to test for colorblindness, as shown in FIG. 9A. In this type of pattern, only select dots among an array of dots are shown in a particular color so as to present a number or letter in that color, which is not visible (or only partially visible) if the viewer is colorblind (or partially colorblind).

Another example of a test pattern that could be employed is an Amsler grid, as shown in FIG. 9B. In this type, if the viewer sees wavy, broken, or blurry lines in the grid, as shown in FIG. 9C, this can be an early indication of macular degeneration.

As yet another example, a test pattern could be employed to evaluate visual acuity. For instance, referring to FIG. 9D, a typical Snellen eye chart may be displayed.

In certain embodiments, the processor (200) described above will also prepare a report based on the results of these tests, which it will then transmit to the remotely located physician. Not only can verbal responses from the patient be communicated to the physician as audio, but these verbal responses can also be converted by the processor (200) into data, which is similarly transmitted to the physician.

Generally, physicians must have access to a billing system with Medicare, Medicaid, or other insurance platform in order to communicate directly or through a billing service. This will allow the physician to receive payment for CPT codes designed to monitor patients at high risk developed on a special patient program. Physicians identify and enroll their at-risk patients in the relevant insurance registry and typically assign a patient coordinator to schedule a preset time with each at-risk patient (e.g., once per week) to be eligible for payment.

It should be understood that the foregoing is illustrative and not limiting, and that obvious modifications may be made by those skilled in the art without departing from the spirit of the invention. Although the invention has been described with reference to embodiments herein, those embodiments do not limit the scope of the invention. Accordingly, reference should be made primarily to the accompanying claims, rather than the foregoing specification, to determine the scope of the invention.

What is claimed is:

1. A method of monitoring an ocular anatomy of a patient, the method comprising:
    receiving an initiation command from a location of the patient;
    transmitting, in response to receiving the initiation command, and over a network, an alert for remote monitoring of the ocular anatomy of the patient to a location of a physician remote from the location of the patient;
    capturing, using a first imaging section including a first imaging sensor at the location of the patient, a plurality of images of the ocular anatomy of the patient, the first imaging section being rotatable such that each of the plurality of images is captured with the first imaging section rotated to a different degree;
    transmitting, over the network, the plurality of images to the location of the physician;
    displaying at least one image of the plurality of images at the location of the physician for determination of whether an in-person examination of the ocular anatomy of the patient is warranted; and
    communicating an instruction from the location of the physician to the location of the patient indicating whether the in-person examination is warranted.

2. The method of claim 1, wherein:
    the initiation command is generated by a personal computing device at the location of the patient;
    the first imaging section is positioned in an ocular imaging unit that connects to the personal computing device; and
    the personal computing device transmits the alert to the location of the physician.

3. The method of claim 2, wherein the initiation command is generated based on an audio command received at the personal computing device.

4. The method of claim 2, wherein the initiation command is generated based on input received on a screen of the personal computing device.

5. The method of claim 2, further comprising:
    storing patient-specific data associated with the patient on the ocular imaging unit,
    wherein transmitting the alert for remote monitoring of the ocular anatomy includes transmitting the patient-specific data with the alert for remote monitoring of the ocular anatomy.

6. The method of claim 5, wherein the patient-specific data comprises physical characteristics of the ocular anatomy of the patient and/or existing medical conditions of the patient.

7. The method of claim 1, wherein the instruction communicated from the location of the physician indicates that the in-person examination is not warranted, the method further comprising:
    receiving a second initiation command from the location of the patient when the patient experiences an adverse event subsequent to the instruction communicated from the location of the physician; and transmitting, in response to receiving the second initiation command, a second alert for remote monitoring of the ocular anatomy of the patient to the location of the physician.

8. The method of claim 1, wherein capturing the plurality of images of the ocular anatomy of the patient is in response to receiving an image capture command from the location of the physician.

9. The method of claim 1, wherein capturing the plurality of images of the ocular anatomy of the patient comprises:
transmitting an instruction from the location of the physician to the location of the patient after the alert is transmitted to the location of the physician; and
after receiving the instruction transmitted from the location of the physician, receiving an image capture command from the patient at the location of the patient.

10. The method of claim 1, wherein the plurality of images comprise live video of the ocular anatomy of the patient transmitted to the location of the physician in real-time.

11. The method of claim 1, wherein the first imaging section includes a first objective lens.

12. The method of claim 11, wherein the first imaging section further includes a rotator that rotates approximately 180 degrees.

13. The method of claim 11, further comprising a second imaging section slidable relative to the first imaging section.

14. The method of claim 13, wherein the second imaging section further comprises an illumination source that directs a fixation light into an optical path of an eye for aligning the eye.

15. The method of claim 13, wherein:
the second imaging section comprises:
a second objective lens;
a display viewable through the second objective lens; and
a display illumination source that directs illumination onto the display to produce a virtual pattern; and
the method further comprises receiving a response from the patient corresponding to the virtual pattern produced on the display.

16. The method of claim 11, wherein:
the first imaging section further comprises an illumination source that illuminates a retina of the patient when the patient looks through the first objective lens, wherein the first imaging sensor captures an image of the retina when the patient looks through the first objective lens and the retina is illuminated.

17. The method of claim 16, wherein the illumination source is a white light or a near infrared light.

18. The method of claim 1, wherein:
the first imaging sensor comprises a plurality of pixels, and
intensity of light received at each of the plurality of pixels is corrected for uneven illumination.

19. The method of claim 1, further comprising determining ocular measurement data based on the plurality of images.

20. The method of claim 19, wherein the ocular measurement data comprises at least one of pupil size or blood vessel diameter.

21. A method of monitoring an ocular anatomy of a patient, the method comprising:
directing, using an illumination source of a second imaging section, a fixation light into an optical path of an eye for aligning the eye;
receiving an initiation command from a location of the patient;
transmitting, in response to receiving the initiation command, and over a network, an alert for remote monitoring of the ocular anatomy of the patient to a location of a physician remote from the location of the patient;
capturing, using a first imaging section including a rotatable first imaging sensor, a plurality of images of the ocular anatomy of the eye by rotating the first imaging sensor to different degrees of rotation;
transmitting, over the network, the plurality of images to the location of the physician;
displaying at least one image of the plurality of images at the location of the physician for determination of whether an in-person examination of the ocular anatomy of the patient is warranted; and
communicating an instruction from the location of the physician to the location of the patient indicating whether the in-person examination is warranted.

22. The method of claim 21, further comprising:
storing patient-specific data associated with the patient, wherein transmitting the alert for remote monitoring of the ocular anatomy includes transmitting the patient-specific data with the alert for remote monitoring of the ocular anatomy.

* * * * *